(12) United States Patent
Nakanishi

(10) Patent No.: US 10,390,773 B2
(45) Date of Patent: Aug. 27, 2019

(54) X-RAY COMPUTED TOMOGRAPHY APPARATUS, A TOP-PLATE CONTROL APPARATUS, AND A TOP-PLATE CONTROL METHOD

(71) Applicant: Toshiba Medical Systems Corporation, Otawara-shi (JP)

(72) Inventor: Satoru Nakanishi, Arlington Heights, IL (US)

(73) Assignee: Canon Medical Systems Corporation, Otawara-shi (JP)

(*) Notice: Subject to any disclaimer, the term of this patent is extended or adjusted under 35 U.S.C. 154(b) by 752 days.

(21) Appl. No.: 14/921,496

(22) Filed: Oct. 23, 2015

(65) Prior Publication Data
US 2016/0038100 A1 Feb. 11, 2016

Related U.S. Application Data

(63) Continuation of application No. PCT/JP2014/063346, filed on May 20, 2014.

(30) Foreign Application Priority Data

May 22, 2013 (JP) .................................. 2013-108185

(51) Int. Cl.
*A61B 6/03* (2006.01)
*A61B 6/04* (2006.01)
(Continued)

(52) U.S. Cl.
CPC .............. *A61B 6/035* (2013.01); *A61B 6/032* (2013.01); *A61B 6/0407* (2013.01); *A61B 6/10* (2013.01);
(Continued)

(58) Field of Classification Search
CPC ....... A61B 6/032; A61B 6/035; A61B 6/0407; A61B 6/0457; A61B 6/102; A61B 6/105;
(Continued)

(56) References Cited

U.S. PATENT DOCUMENTS 6,834,097 B2* 12/2004 Yamazaki .............. A61B 6/488
378/19
6,922,457 B2* 7/2005 Nagata ................... A61B 6/032
378/15
(Continued)

FOREIGN PATENT DOCUMENTS

JP 63-049141 A 3/1988
JP 2010-284303 A 12/2010

OTHER PUBLICATIONS

International Search Report dated Jun. 17, 2014 in PCT/JP2014/063346 filed May 20, 2014, with English translation.
(Continued)

*Primary Examiner* — Allen C. Ho
(74) *Attorney, Agent, or Firm* — Oblon, McClelland, Maier & Neustadt, L.L.P.

(57) ABSTRACT

According to embodiment, an X-ray computed tomography apparatus includes a gantry, bed, input interface circuitry, and control circuitry. The gantry includes an X-ray tube generating X-rays and an X-ray detector detecting the X-rays transmitted through a subject. The bed arranged at a front surface side of the gantry includes a top plate moving toward an opening of the gantry. The input interface circuitry inputs an imaging plan concerning imaging of the subject. The control circuitry controls the bed to limit movement of the top plate when the input interface circuitry inputs an imaging plan to image part of the subject inserted from a back surface side of the gantry into the opening.

12 Claims, 8 Drawing Sheets

(51) Int. Cl.
*A61B 6/00* (2006.01)
*A61B 6/10* (2006.01)

(52) U.S. Cl.
CPC .............. *A61B 6/102* (2013.01); *A61B 6/105* (2013.01); *A61B 6/46* (2013.01); *A61B 6/461* (2013.01); *A61B 6/467* (2013.01); *A61B 6/0457* (2013.01)

(58) Field of Classification Search
CPC ........... A61B 6/46; A61B 6/461; A61B 6/467; A61B 6/10
USPC .................. 378/4, 20, 91, 95, 209, 204–206
See application file for complete search history.

(56) References Cited

U.S. PATENT DOCUMENTS

| | | | | |
|---|---|---|---|---|
| 6,942,385 B2* | 9/2005 | Fadler | .............. | A61B 6/08 378/205 |
| 6,944,261 B2* | 9/2005 | Adachi | .............. | A61B 6/032 378/20 |
| 6,955,464 B1* | 10/2005 | Tybinkowski | ....... | A61B 6/0457 108/143 |
| 6,990,170 B2* | 1/2006 | Sugihara | .............. | A61B 6/032 378/15 |
| 7,085,343 B2* | 8/2006 | Shinno | .............. | A61B 6/032 378/19 |
| 7,103,134 B2* | 9/2006 | Suzuki | .............. | A61B 6/032 378/4 |
| 7,139,368 B2* | 11/2006 | Kawanabe | .............. | A61B 6/032 378/162 |
| 7,154,988 B2* | 12/2006 | Sugihara | .............. | A61B 6/032 378/15 |
| 7,177,386 B2* | 2/2007 | Mostafavi | .............. | A61B 5/1135 378/4 |
| 7,215,733 B2* | 5/2007 | Nabatame | .............. | A61B 6/032 378/110 |
| 7,242,749 B2* | 7/2007 | Hsieh | .............. | A61B 6/032 378/15 |
| 7,384,194 B2* | 6/2008 | Gatten | .............. | G01N 23/046 378/20 |
| 7,480,362 B2* | 1/2009 | Carmi | .............. | A61B 6/032 378/19 |
| 7,648,273 B2* | 1/2010 | Manzke | .............. | A61B 6/107 250/515.1 |
| 7,822,173 B2* | 10/2010 | Mattson | .............. | A61B 6/585 378/19 |
| 7,933,376 B2* | 4/2011 | Yoda | .............. | A61B 6/04 378/205 |
| 8,170,176 B2* | 5/2012 | Soejima | .............. | A61B 6/032 378/20 |
| 8,243,874 B2* | 8/2012 | Carmi | .............. | G01T 1/2985 250/366 |
| 8,320,520 B2* | 11/2012 | Kondo | .............. | A61B 6/032 378/15 |
| 8,382,372 B2* | 2/2013 | Maschke | .............. | A61B 5/06 378/162 |
| 8,681,933 B2* | 3/2014 | Suzuki | .............. | A61B 6/0457 378/146 |
| 8,841,619 B2* | 9/2014 | Volokh | .............. | A61B 6/037 250/363.05 |
| 8,885,902 B2* | 11/2014 | Shechter | .............. | G06T 11/005 382/128 |
| 8,939,920 B2* | 1/2015 | Maad | .............. | A61B 6/0457 600/595 |
| 9,028,144 B2* | 5/2015 | Choi | .............. | A61B 6/032 378/205 |
| 9,050,055 B2* | 6/2015 | Korporaal | .............. | A61B 6/481 |
| 9,078,618 B2* | 7/2015 | Stern | .............. | A61B 6/037 |
| 9,161,726 B2* | 10/2015 | Dong | .............. | A61B 6/035 |
| 9,271,681 B2* | 3/2016 | Uebayashi | .............. | A61B 6/032 |
| 9,389,190 B2* | 7/2016 | Tsuyuki | .............. | G01N 23/046 |
| 9,480,443 B2* | 11/2016 | Feuerlein | .............. | A61B 6/032 |
| 9,662,075 B2* | 5/2017 | Liu | .............. | A61B 6/032 |
| 9,706,969 B2* | 7/2017 | Takei | .............. | A61B 6/488 |
| 9,757,075 B2* | 9/2017 | Mukumoto | .............. | A61B 6/03 |
| 9,865,060 B2* | 1/2018 | Mukumoto | .............. | G06T 7/35 |
| 9,872,658 B2* | 1/2018 | Yamada | .............. | A61B 6/032 |
| 9,901,310 B2* | 2/2018 | Uhlemann | .............. | A61B 5/0507 |
| 9,913,996 B2* | 3/2018 | Takahashi | .............. | G01B 11/002 |
| 10,022,100 B2* | 7/2018 | Iijima | .............. | A61B 6/4441 |

OTHER PUBLICATIONS

Written Opinion dated Jun. 17, 2014 in PCT/JP2014/063346 filed May 20, 2014.

\* cited by examiner

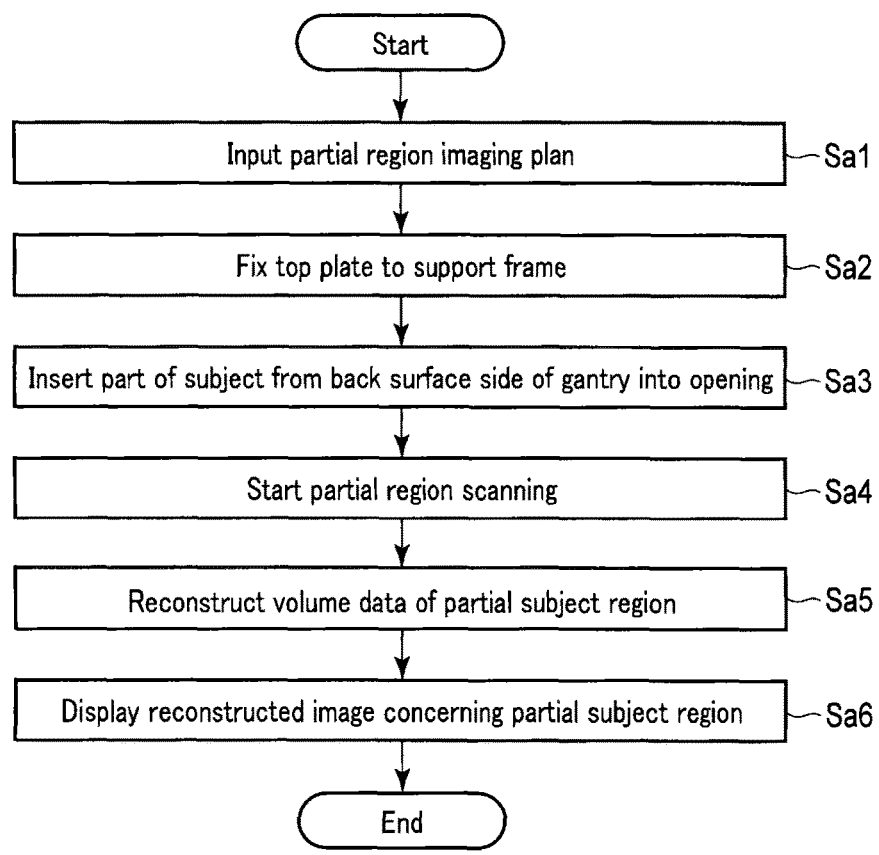
F I G. 2

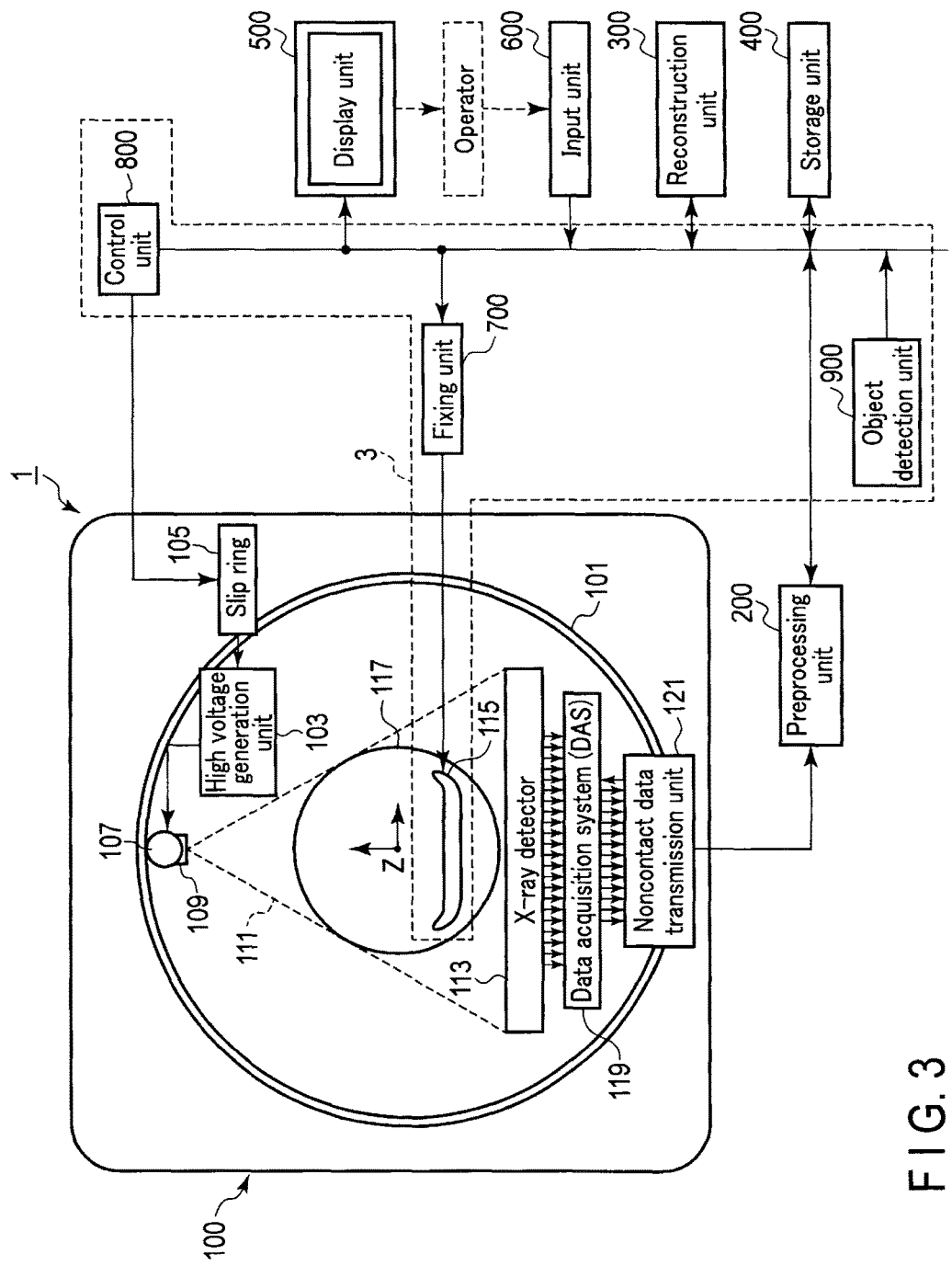
F I G. 3

X-RAY COMPUTED TOMOGRAPHY APPARATUS, A TOP-PLATE CONTROL APPARATUS, AND A TOP-PLATE CONTROL METHOD

CROSS-REFERENCE TO RELATED APPLICATIONS

This application is a Continuation Application of PCT Application No. PCT/JP2014/063346, filed May 20, 2014 and based upon and claims the benefit of priority from the Japanese Patent Application No. 2013-108185, filed May 22, 2013, the entire contents of which are incorporated herein by reference.

FIELD

Embodiments described herein relate generally to an x ray computed tomography apparatus, a top plate control apparatus and a top plate control method.

BACKGROUND

When using a conventional X-ray computed tomography (to be referred to as CT hereinafter) apparatus, a subject is generally placed on a top plate, as shown in FIG. 8. The X-ray CT apparatus then executes imaging (to be referred to as regular imaging hereinafter). In regular imaging for a subject, the opening portion of the gantry is sometimes provided with a contact sensor to prevent the subject from being caught between the top plate and the gantry. The X-ray CT apparatus has an interlock mechanism which forcibly stops the movement of the top plate or gantry if the subject comes into contact with the opening portion of the gantry.

Recent X-ray CT apparatuses have area detectors. Such an X-ray CT apparatus having an area detector (to be referred to as an ADCT apparatus hereinafter) sometimes images a desired imaging region (e.g., a portion concerning swallowing or a wrist joint portion) while the subject is placed at the back surface side of the gantry (to be referred to as the gantry back hereinafter) and the imaging region is inserted by the operator into a field of view (to be referred to as an FOV hereinafter) in the opening portion of the gantry.

When performing volume imaging of part of the subject placed at the gantry back, the above interlock mechanism does not work, as shown in FIG. 9. More specifically, when imaging a subject placed at the gantry back, the top plate may damage the subject at the gantry back upon movement of the top plate regardless of an operator's intention. The above problem occurs when, for example, the operator erroneously selects an imaging plan concerning helical imaging and the apparatus executes imaging while a subject is placed at the gantry back.

BRIEF DESCRIPTION OF DRAWINGS

FIG. 2 is a flowchart showing an example of a procedure for top plate fixing processing according to the first embodiment.

FIG. 3 is a block diagram showing the arrangement of an X-ray computed tomography apparatus according to the second embodiment.

DETAILED DESCRIPTION

Figure 1:
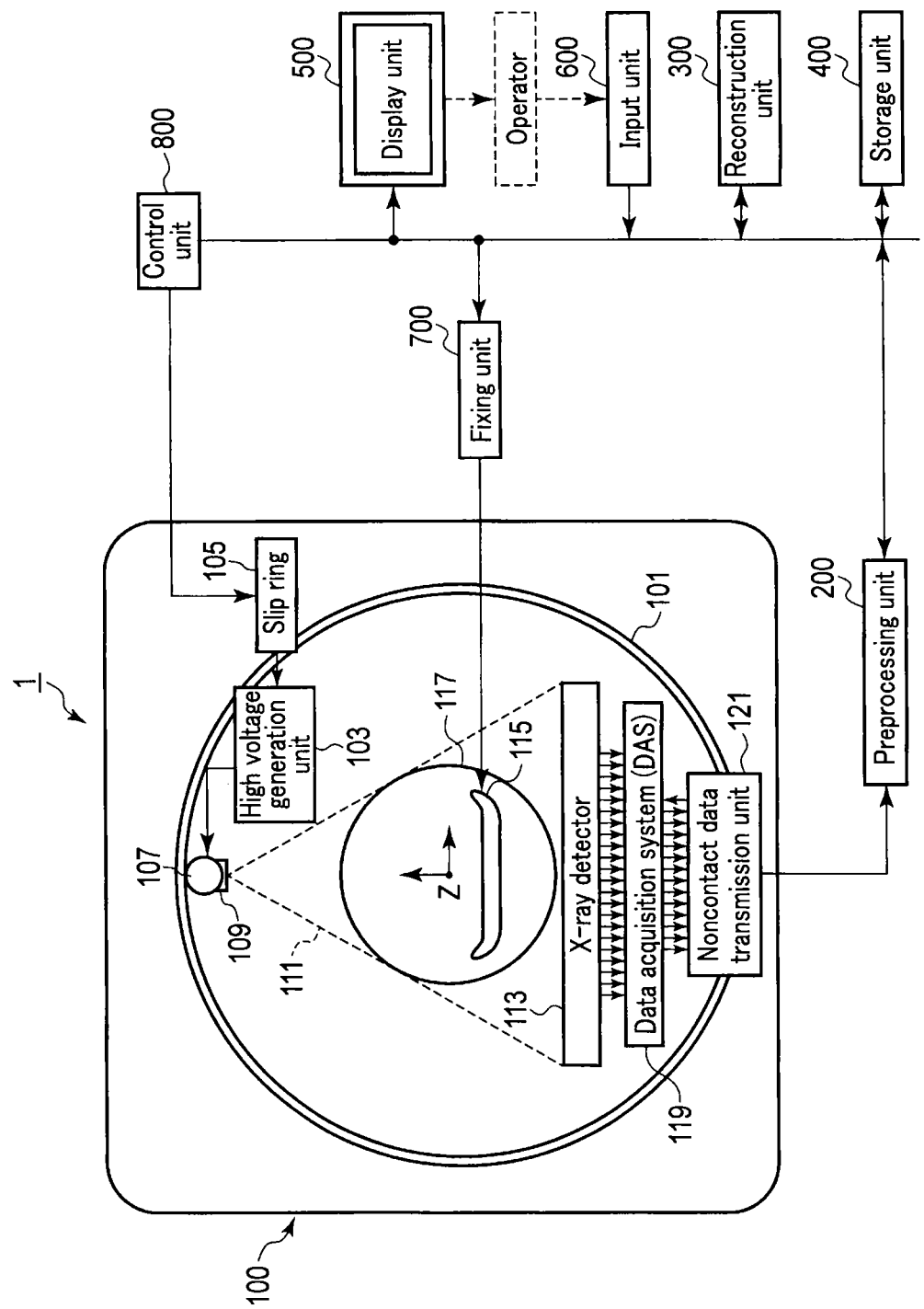
FIG. 1 is a block diagram showing the arrangement of an X-ray computed tomography apparatus according to the first embodiment.

In general, according to one embodiment, an X-ray computed tomography apparatus includes a gantry, bed, input interface circuitry, and control circuitry. The gantry includes an X-ray tube generating X-rays and an X-ray detector detecting the X-rays transmitted through a subject. The bed arranged at a front surface side of the gantry includes a top plate moving toward an opening of the gantry. The input interface circuitry inputs an imaging plan concerning imaging of the subject. The control circuitry controls the bed to limit movement of the top plate when the input interface circuitry inputs an imaging plan to image part of the subject inserted from a back surface side of the gantry into the opening.

An X-ray computed tomography apparatus (to be also referred to as an X-ray CT apparatus) according to an embodiment will be described below with reference to the accompanying drawings. Note that X-ray computed tomography apparatuses include various types of apparatuses, e.g., a rotate/rotate-type apparatus in which an X-ray tube and an X-ray detector rotate together around a subject and a stationary/rotate-type apparatus in which many X-ray detection elements arrayed in the form of a ring are fixed, and only the X-ray tube rotates around a subject. Either type can be applied to this embodiment.

In addition, in order to reconstruct an image, projection data corresponding to one rotation around a subject, i.e., 360°, is required, or (180°+fan angle) projection data is required in the half scan method. Either reconstruction scheme can be applied to this embodiment. As mechanisms of changing incident X-rays into charge, the following techniques are the mainstream: an indirect conversion type that converts X-rays into light through a phosphor such as a scintillator and converts the light into charge through photoelectric conversion elements such as photodiodes, and a direct conversion type that uses generation of electron-hole pairs in a semiconductor such as selenium by X-rays and migration of the electron-hole pairs to an electrode, i.e., a photoconductive phenomenon. As an X-ray detection element, either of these schemes can be used.

Furthermore, in recent years, with advances toward the commercialization of a so-called multi-tube type X-ray computed tomography apparatus having a plurality of pairs of X-ray tubes and X-ray detectors mounted on a rotating frame, related techniques have been developed. This embodiment can be applied to both a conventional single-tube type X-ray computed tomography apparatus and a multi-tube type X-ray computed tomography apparatus. When using a multi-tube type X-ray computed tomography apparatus, different tube voltages are respectively applied to a plurality of tubes (multi-tube scheme). The single-tube type X-ray computed tomography apparatus will be exemplified here.

In addition, each X-ray detection element may be a two-layer detection element having a front-surface detection portion which detects low-energy X-rays and a rear-surface detection portion which is provided on the rear surface of the front-surface detector to detect high-energy X-rays. In this case, for the sake of simplicity, assume that the X-ray detector uses one-layer X-ray detection elements.

Note that the same reference numerals in the following description denote constituent elements having almost the same functions and arrangements, and a repetitive description will be made only when required.

First Embodiment

FIG. 1 shows the arrangement of an X-ray computed tomography apparatus 1 according to this embodiment. The X-ray computed tomography apparatus 1 includes a gantry 100, a preprocessing unit 200, a reconstruction unit 300, a storage unit 400, a display unit 500, an input unit 600, a fixing unit 700, and a control unit 800. Note that the X-ray computed tomography apparatus 1 may include a interface (to be referred to as an I/F hereinafter) (not shown). The I/F connects the X-ray computed tomography apparatus 1 to an electronic communication line (to be referred to as a network hereinafter). A radiology department information management system, a hospital information system, and other medical image diagnostic apparatuses (none of which are shown) are connected to the network.

The gantry 100 accommodates a rotating support mechanism (not shown). The rotating support mechanism includes a rotating frame 101, a frame support mechanism which supports the rotating frame 101 so as to make it rotatable about a rotation axis Z, and a rotation driving unit (electric motor) (not shown) which drives the rotation of the rotating frame 101.

The rotating frame 101 is equipped with a high voltage generation unit 103, an X-ray tube 107, a collimator unit 109, an X-ray detector (to be referred to as an area detector) 113 which is also called a two-dimensional array type or multi-array type detector, a data acquisition system (to be referred to as a DAS hereinafter) 119, a noncontact data transmission unit 121, a cooling device (not shown), a gantry controller (not shown), and the like.

The high voltage generation unit 103 generates a tube voltage to be applied to the X-ray tube 107 and a tube current to be supplied to the X-ray tube 107 by using the power supplied via a slip ring 105 under the control of the control unit 800 (to be described later). Note that the high voltage generation unit 103 may be provided outside the gantry 100. In this case, the high voltage generation unit 103 applies a tube voltage to the X-ray tube 107 and supplies a tube current to the X-ray tube 107 via the slip ring 105.

The X-ray tube 107 emits X-rays from the X-ray focus upon receiving the tube voltage applied from the high voltage generation unit 103 and the tube current supplied from it.

The collimator unit 109 is attached to the X-ray radiation window provided on the front surface of the X-ray tube 107.

The collimator unit 109 has a plurality of collimator plates. The plurality of collimator plates shape X-rays emerging from the X-ray focus into, for example, a cone beam shape (pyramidal shape). More specifically, the control unit 800 (to be described later) drives the plurality of collimator plates to obtain a cone angle so as to obtain projection data with a preset slice thickness by actual measurement. The cone-angle-related aperture widths of at least two collimator plates (to be referred to as cone angle collimators hereinafter) of the plurality of collimator plates are independently driven under the control of the control unit 800.

A dotted line 111 in FIG. 1 indicates an X-ray radiation range. The X-axis is a straight line which is perpendicular to the rotation axis Z and extends upward in the vertical direction. The Y-axis is a straight line perpendicular to the X-axis and the rotation axis Z.

The area detector 113 detects X-rays transmitted through a subject. The area detector 113 is attached at a position and angle at which it faces the X-ray tube 107 through the rotation axis Z. The area detector 113 includes a plurality of X-ray detection elements. Assume that in the following description, a single X-ray detection element forms a single channel. A plurality of channels are two-dimensionally arranged in two directions, i.e., the slice direction and the arc direction (channel direction) which is perpendicular to the rotation axis Z and whose radius matches the distance from an X-ray focus, as a center, from which X-rays emerge, to the center of the light-receiving portion of an X-ray detection element corresponding to one channel. The two-dimensional array is formed by arranging a plurality of channels, one-dimensionally arrayed along the channel direction, in the form of a plurality of columns arranged in the slice direction.

The area detector 113 having such two-dimensional array of X-ray detection elements may be formed by arranging a plurality of modules, one-dimensionally arrayed in a nearly arc direction, in the form of a plurality of columns in the slice direction. In addition, the area detector 113 may be constituted by a plurality of modules each having a plurality of X-ray detection elements arrayed in one column. In this case, the respective modules are one-dimensionally arrayed in the nearly arc direction along the above channel direction. The number of X-ray detection elements arranged in the slice direction is called the number of columns.

When performing regular imaging or scanning (to be referred to as regular scanning hereinafter), a subject is placed on a top plate 115. The top plate 115 on which the subject is placed is inserted from the front surface side of the gantry 100 (on the side of the gantry 100 on which the bed (to be described later) is arranged) into the cylindrical imaging area between the X-ray tube 107 and the area detector 113.

When imaging or scanning (to be referred to as partial region scanning hereinafter) a partial region of a subject (to be referred to as a partial subject region hereinafter) such as a region concerning swallowing or a limb joint region, the subject is placed at the back surface side of the gantry 100, i.e., on the opposite side of the gantry to the bed. The partial subject region is then inserted from the back surface side of the gantry 100 into the imaging area.

The data acquisition system (to be referred to as a DAS hereinafter) 119 is connected to the output side of the area detector 113. The DAS 119 is provided, for each channel, with an I-V converter which converts a current signal from each channel of the area detector 113 into a voltage, an integrator which periodically integrates these voltage signals in synchronism with an X-ray irradiation period, an amplifier which amplifies an output signal from the integrator, and an analog/digital converter which converts an output signal from the amplifier into a digital signal. The DAS 119 changes the integration interval of the integrator in accordance with a scan under the control of the control unit 800 (to be described later). The DAS 119 outputs data (pure raw data) to the preprocessing unit 200 via the noncontact data transmission unit 121 using magnetic transmission/reception or optical transmission/reception.

The preprocessing unit 200 performs preprocessing for the pure raw data output from the DAS 119. The preprocessing unit 200 performs preprocessing such as sensitivity nonuniformity correction between channels and correction of an extreme decrease in signal intensity or signal dropout caused by an X-ray strong absorber, mainly a metal portion. The data (called raw data or projection data; projection data in this case) output from the preprocessing unit 200 immediately before reconstruction processing is stored in the storage unit 400 including a magnetic disk, magneto-optical disk, or semiconductor memory in association with view angles at the time of data acquisition.

For the sake of descriptive convenience, a set of projection data throughout a plurality of channels which are almost simultaneously acquired and interpolated by one shot at the same view angle and defined by a cone angle will be referred to as a projection data set. View angles are represented by angles in the range of 0° to 360° which represent the respective positions on a circular orbit centered on the rotation axis Z, along which the X-ray tube 107 revolves, with the angle of the uppermost portion on the circular orbit in an upward vertical direction from the rotation axis Z being 0°. Note that projection data of a projection data set which corresponds to each channel is identified by a view angle, cone angle, and channel number.

The reconstruction unit 300 has a function of reconstructing a nearly cylindrical three-dimensional image (volume data) concerning a reconstruction region by the Feldkamp method or the cone beam reconstruction method based on a projection data set acquired at view angles in the range of 360° or 180°+fan angle. The reconstruction unit 300 also has a function of reconstructing a two-dimensional image (tomographic image) by, for example, the fan beam reconstruction method (also called the fan beam convolution back projection method) or the filtered back projection method. The Feldkamp method is a reconstruction method to be used when projection rays intersect a reconstruction plane like a cone beam. The Feldkamp method is an approximate image reconstruction method of performing convolution by regarding a projection beam as a fan projection beam on the premise that the cone angle is small, and performing back projection in a scan along a ray. The cone beam reconstruction method is a reconstruction method which corrects projection data in accordance with the angle of a ray relative to a reconstruction plane. This method suppresses cone angle errors more than the Feldkamp method.

The storage unit 400 stores medical images (to be referred to as reconstructed images hereinafter) reconstructed by the reconstruction unit 300, a plurality of projection data sets, and the like. The storage unit 400 stores operator's instructions, image processing conditions, imaging conditions, and the like which are input from the input unit 600 (to be described later). The storage unit 400 stores control programs for controlling the gantry 100, the bed (to be described later), and the like for the X-ray computed tomography apparatus.

The display unit 500 displays the medical image reconstructed by the reconstruction unit 300, a scanogram, and an input screen for inputting scan conditions to be set for X-ray computed tomography, reconstruction conditions associated with reconstruction processing, and the like. Note that the display unit 500 may also display the imaging plan input via the input unit 600 (to be described later).

The input unit 600 inputs various types of instructions, commands, information, selections, and settings from the operator to the X-ray computed tomography apparatus 1. The input instructions, commands, information, selections, and settings are output to the control unit 800 (to be described later). Although not shown, the input unit 600 includes a trackball, switch buttons, a mouse, and a keyboard for, for example, setting an ROI (Region Of Interest). The input unit 600 inputs a scan range for the scanogram generated and displayed by imaging (to be referred to as scanography hereinafter) for deciding a scan start position, imaging conditions, and the like for a subject.

The input unit 600 detects the coordinates of the cursor displayed on a display screen, and outputs the detected coordinates to the control unit 800. Note that the input unit 600 may be a touch panel provided to cover the display screen. In this case, the input unit 600 detects touched and designated coordinates by a coordinate reading principle such as an electromagnetic induction scheme, magnetostriction scheme, or a pressure-sensitive scheme, and outputs the detected coordinates to the control unit 800.

The input unit 600 inputs a scan plan for a subject. More specifically, the input unit 600 inputs at least one of a plurality of imaging plans concerning a regular scan, a helical scan, and a partial region scan. When an imaging plan concerning a partial region scan (to be referred to as a partial region imaging plan hereinafter) is input in accordance with an operator's instruction, the input unit 600 outputs a predetermined signal corresponding to the partial region imaging plan to the fixing unit 700 (to be described later). In general, a partial region imaging plan is an imaging plan for imaging part of a subject upon inserting the part from the back surface side of the gantry 100 into a field of view in an opening 117.

Note that the input unit 600 may input a limit instruction to limit the movement of the top plate 115. At this time, for example, the display unit 500 displays a partial imaging plan. In addition, the input unit 600 may output information corresponding to the input imaging plan to the display unit 500 and the control unit 800. The input unit 600 may also output a predetermined signal or a signal concerning the limit instruction to the control unit 800. Furthermore, of the input unit 600, an input device (a manual lock button or the like) concerning an input to limit the movement of the top plate 115 may be provided on the bed (to be described later) or the top plate 115.

The bed (not shown) includes the top plate 115, a support frame (not shown) which supports the top plate 115 so as to make it movable along the Z direction, the fixing unit 700 which fixes the top plate 115 to the support frame, and a driving unit (not shown) which drives the top plate 115 and the bed.

Note that the bed may include an input device (input unit 600) such as a switch button for limiting the movement of the top plate 115. The input device is provided on, for example, the upper surface (or a side surface) of the bed or the upper surface (or a side surface) of the top plate 115. In this case, the movement of the top plate 115 is limited by an operation on the input device by the operator or the control of the control unit 800 on the bed. For example, the operation of limiting the movement of the top plate 115 includes inhibiting the top plate 115 from moving from the front surface side of the gantry 100 to the opening 117. At this time, for example, the movement range of the top plate 115 is limited to the range from the opening 117 on the gantry front surface side to the bed side. Note that the operation of limiting the movement of the top plate 115 may include limiting the movement of the top plate 115 in the vertical direction by the driving unit (to be described later).

The driving unit moves the bed up and down in accordance with an operator's instruction. The driving unit moves the top plate 115 along the Z direction in accordance with the imaging plan input by the input unit 600.

Upon receiving a partial region imaging plan via the input unit 600, the fixing unit 700 fixes the top plate 115 to the support frame. More specifically, upon receiving a predetermined signal output from the input unit 600, the fixing unit 700 fixes the top plate 115 to the support frame. That is, upon receiving a partial region imaging plan via the input unit 600, the fixing unit 700 fixes the top plate 115 to the support frame. This fixes the top plate 115 to the support frame.

Note that the fixing unit 700 may fix the top plate 115 to the support frame so as to limit the movement of the top plate 115 under the control of the control unit 800 in response to the input of a partial imaging plan or limit instruction. Alternatively, the fixing unit 700 may fix the top plate 115 to the support frame so as to limit the movement of the top plate 115 in accordance with an operation (the input of a limit instruction) on the input device provided on the bed or the top plate 115.

The control unit 800 functions as the main unit of the X-ray computed tomography apparatus 1. The control unit 800 includes a CPU and a memory (neither of which is shown). The control unit 800 controls the high voltage generation unit 103, the gantry 100, and the like to perform X-ray computed tomography of a subject based on examination schedule data and control programs stored in a memory (not shown). More specifically, the control unit 800 temporarily stores an operator's instruction or the like sent from the input unit 600 and the like in the memory (not shown). The control unit 800 controls the high voltage generation unit 103, the gantry 100, and the like based on information temporarily stored in the memory. The control unit 800 reads out control programs for executing predetermined image generation processing/displaying processing and the like from the storage unit 400 and loads them in its own memory, thereby executing computation/processing and the like concerning various types of processing.

Note that upon receiving a partial region imaging plan via the input unit 600, the control unit 800 may control the fixing unit 700 to fix the top plate 115 to the support frame. For example, upon receiving a partial imaging plan from the input unit 600, the control unit 800 controls the bed to limit the movement of the top plate 115.

(Top Plate Fixing Function)

The top plate fixing function is a function of fixing the top plate 115 to the support frame when a partial region imaging plan is input via the input unit 600. Processing concerning the top plate fixing function (to be referred to as top plate fixing processing hereinafter) will be described below.

FIG. 2 is a flowchart showing an example of a top plate fixing processing procedure.

A partial region imaging plan is input via the input unit 600 (step Sa1). At this time, the display unit 500 may display the partial imaging plan. The bed is controlled to limit the movement range of the top plate 115 under the control of the control unit 800. For example, the top plate 115 is fixed to the support frame in accordance with a predetermined signal output from the input unit 600 (step Sa2).

Part of the subject is inserted from the back surface side of the gantry 100 into the field of view in the opening 117 (step Sa3). A partial region scan is executed (step Sa4).

The reconstruction unit 300 reconstructs volume data concerning the partial subject region based on the projection data set output from the preprocessing unit 200 (step Sa5). The display unit 500 displays a reconstructed image concerning the partial subject region (step Sa6).

According to the above arrangement, the following effects can be obtained.

The X-ray computed tomography apparatus 1 according to this embodiment can limit the movement of the top plate 115 in accordance with the partial region imaging plan (dedicated imaging plan) input via the input unit 600. For example, inputting the partial region imaging plan can fix the top plate 115 to the support frame. This makes it possible to secure the safety of a subject when scanning a partial subject region upon inserting part of the subject from the back surface side of the gantry 100 into the field of view. That is, a partial region imaging plan is selected, it is possible to prevent the top plate 115 from moving regardless of the operator's intention.

In addition, the X-ray computed tomography apparatus 1 according to this embodiment displays the imaging plan input via the input unit 600 and can control the bed to limit the movement of the top plate 115 in response to the input of a limit instruction via the input unit 600. This informs the operator of the input (selected) imaging plan and decides whether to limit the movement of the top plate 115 in accordance with the determination made by the operator. Informing the operator of the imaging plan can present the operator with the risk associated with the movement of the top plate 115.

As described above, this embodiment can image part of a subject from the back surface side of the gantry 100 while securing the safety of the subject.

Second Embodiment

A difference from the first embodiment is that when an object placed at the back surface side of a gantry 100 is detected, a top plate 115 is fixed to the support frame.

FIG. 3 is a block diagram showing the arrangement of an X-ray computed tomography apparatus 1 according to the second embodiment. The X-ray computed tomography apparatus 1 according to the second embodiment includes the gantry 100, a preprocessing unit 200, a reconstruction unit 300, a storage unit 400, a display unit 500, an input unit 600, a fixing unit 700, a control unit 800, and an object detection unit 900.

The object detection unit 900 detects an object placed at the back surface side of the gantry 100. Upon detecting an object, the object detection unit 900 outputs an object detection signal to the fixing unit 700. More specifically, the object detection unit 900 detects an object placed at the back surface side of the gantry 100 in the movement range of the top plate 115 (to be referred to as the top plate movement range hereinafter) by touching the object. The object detection unit 900 is a touch sensor provided on the mounting surface of the gantry 100 throughout the top plate movement range. The area of the touch sensor corresponds to an area corresponding to the top plate movement range at the back surface side of the gantry 100. The touch sensor is a pressure-sensitive switch such as a mat switch. An object is an arbitrary object such as a subject, a helper who helps the subject, an injector connected to the subject, a chair which holds the subject in a sitting position, or a stretcher.

Note that the object detection unit 900 can be anything as long as it has a mechanism which can detect an object placed at the back surface side of the gantry 100 within a predetermined distance.

The fixing unit 700 fixes the top plate 115 to the support frame in accordance with the input of an object detection signal output from the object detection unit 900.

Figure 4:
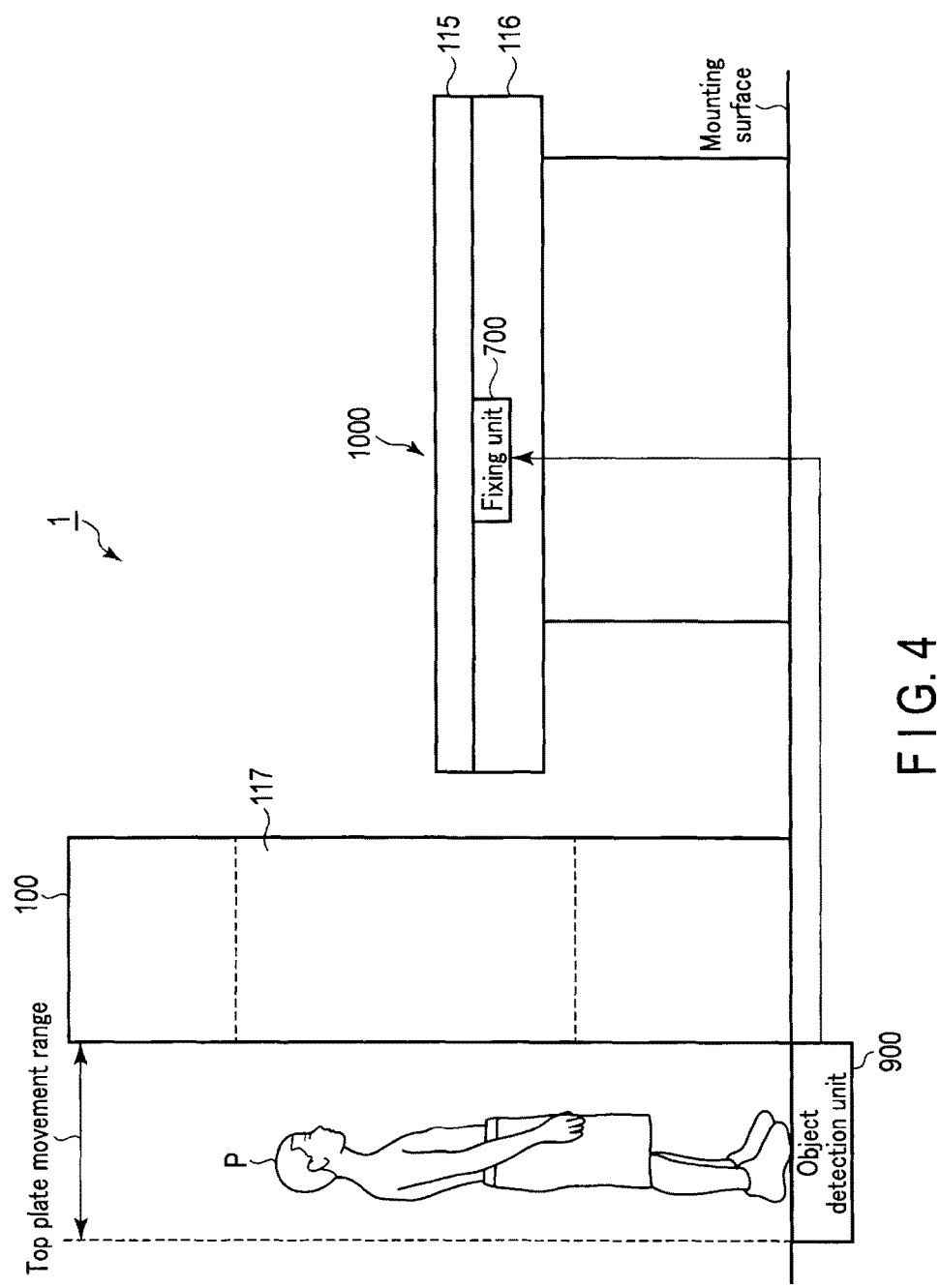
FIG. 4 is a view showing, together with the gantry and the bed, a subject P placed at the back surface side of a gantry according to the second embodiment.

FIG. 4 is a view showing, together with the gantry 100 and a bed 1000, the subject P placed at the back surface side of the gantry 100. As shown in FIG. 4, when a subject P (or object) is placed in the top plate movement range, the object detection unit 900 placed on the mounting surface of the gantry 100 or bed 1000 detects the pressure applied by the subject P (object). As shown in FIG. 4, the object detection unit 900 outputs an object detection signal to the fixing unit 700 via a wire provided below the mounting surface. The fixing unit 700 fixes the top plate 115 to a support frame 116 in response to the arrival of an object detection signal.

(Top Plate Fixing Function)

The top plate fixing function according to this embodiment is a function of fixing the top plate 115 to the support frame 116 in accordance with an object detection signal concerning an object detected by the object detection unit 900. Processing concerning the top plate fixing function (to be referred to as top plate fixing processing hereinafter) will be described below.

Figure 5:
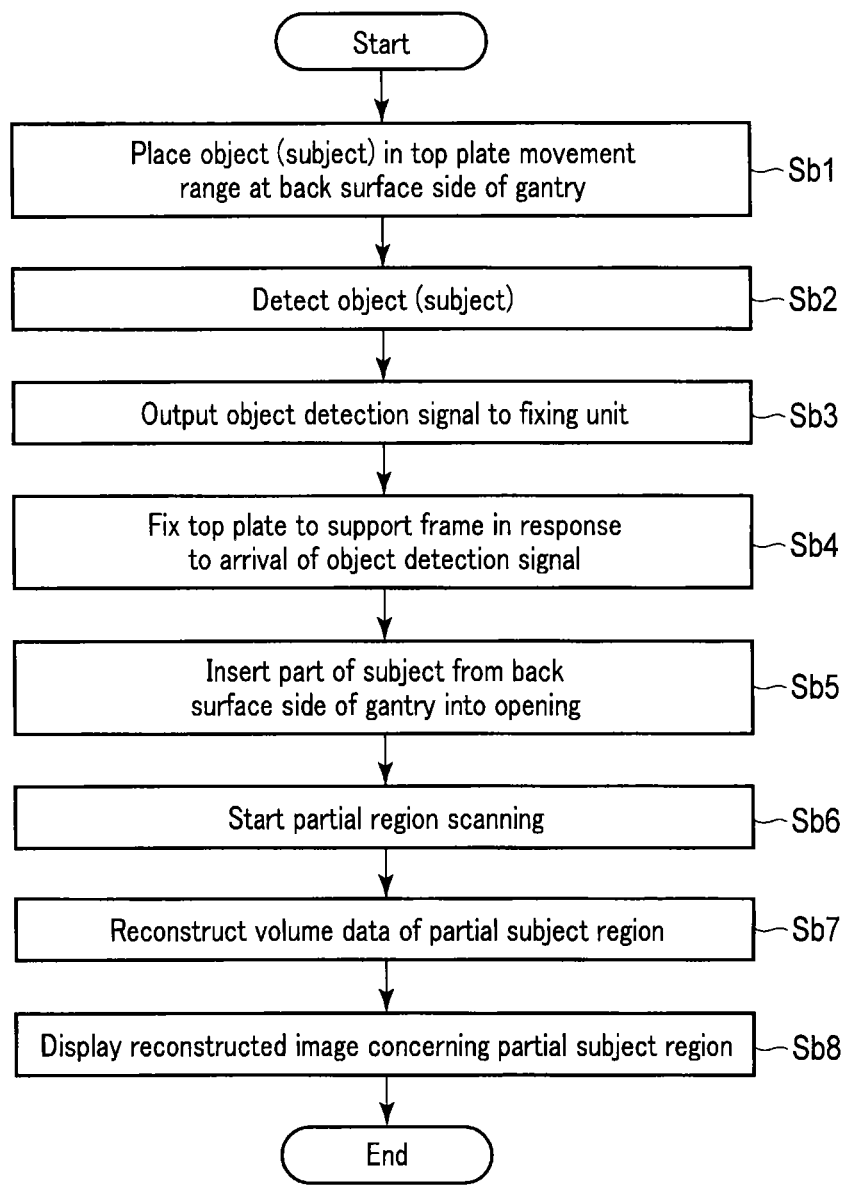
FIG. 5 is a flowchart showing an example of a procedure for top plate fixing processing according to the second embodiment.

FIG. 5 is a flowchart showing an example of a procedure for top plate fixing processing.

An object is placed in the top plate movement range at the back surface side of the gantry 100 (step Sb1). The object detection unit 900 detects the placed object (step Sb2). The object detection unit 900 generates an object detection signal. The object detection unit 900 outputs the generated object detection signal to the fixing unit 700 (step Sb3). The top plate 115 is fixed to the support frame 116 in response to the arrival of the object detection signal at the fixing unit 700 (step Sb4).

Part of the subject is inserted from the back surface side of the gantry 100 into the field of view in an opening 117 (step Sb5). A partial region scan is executed (step Sb6). The reconstruction unit 300 reconstructs volume data concerning the partial subject region based on the projection data set output from the preprocessing unit 200 (step Sb7). The display unit 500 displays a reconstructed image concerning the partial subject region (step Sb8).

(First Modification)

A difference from the second embodiment is that the object detection unit 900 is provided on the exterior of the gantry 100 at the back surface side of the gantry 100.

The object detection unit 900 is provided on the exterior of the gantry 100 at the back surface side of the gantry 100. The object detection unit 900 is, for example, an infrared sensor or ultrasonic sensor. In this modification, the object detection unit 900 is generally a sensor using a predetermined electromagnetic wave or a predetermined sound wave. The range of object detection by the object detection unit 900 corresponds to the top plate movement range.

The predetermined electromagnetic wave is, for example, infrared light. In this case, the object detection unit 900 is an infrared sensor. Note that the predetermined electromagnetic wave is not limited to infrared light and may be an electromagnetic wave having an arbitrary wavelength. In addition, the predetermined sound wave is, for example, an ultrasonic wave. In this case, the object detection unit 900 is an ultrasonic sensor. Note that the predetermined sound wave is not limited to an ultrasonic wave and may be a sound wave having an arbitrary wavelength.

Figure 6:
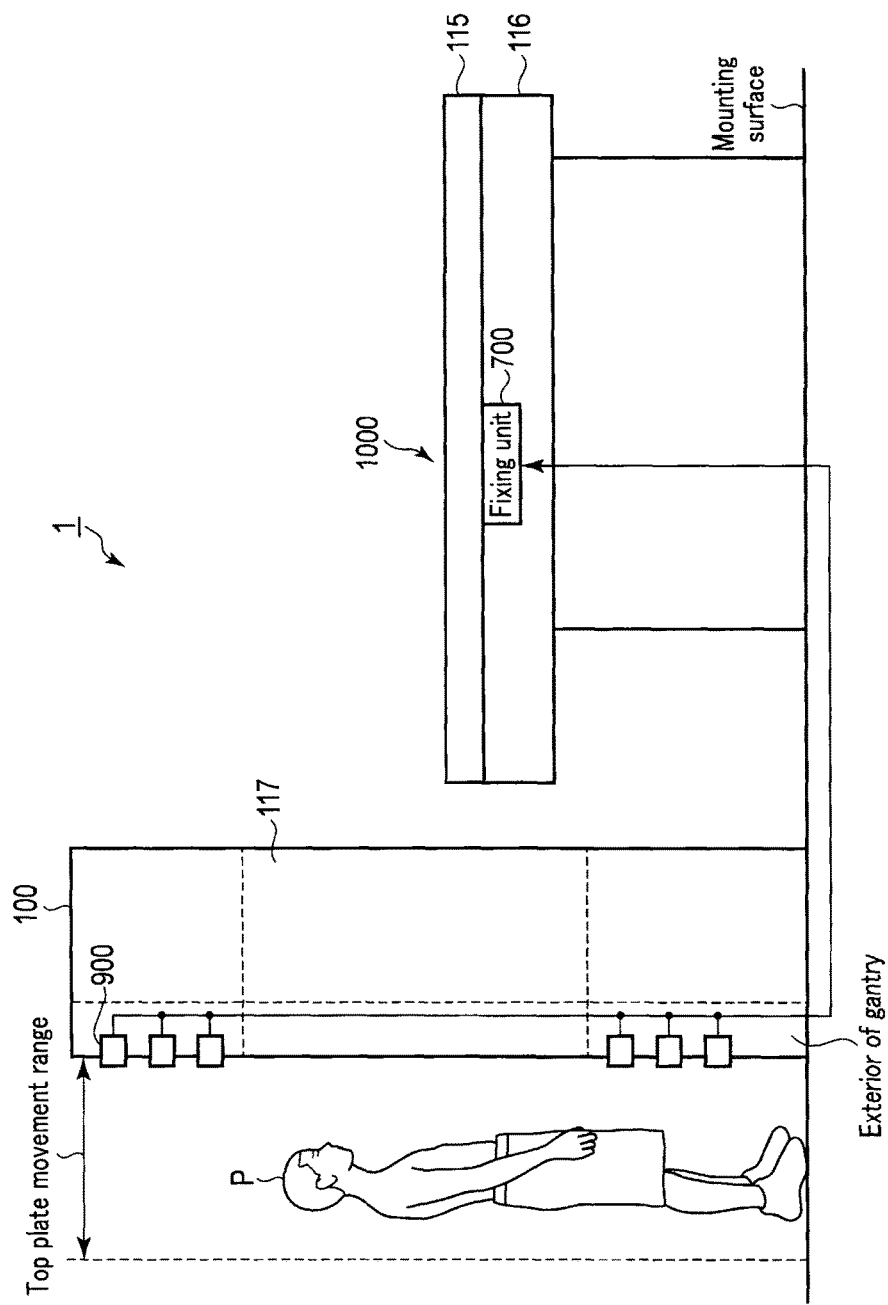
FIG. 6 is a view showing, together with the gantry and the bed, the subject P placed at the back surface side of the gantry according to the first modification of the second embodiment.

FIG. 6 is a view showing, together with the gantry 100 and the bed 1000, the subject P placed at the back surface side of the gantry 100. As shown in FIG. 6, when a subject P (or object) is placed within the top plate movement range, the object detection unit 900 provided on the exterior of the gantry 100 at the back surface side of the gantry 100 detects the subject P. As shown in FIG. 6, the object detection unit 900 outputs an object detection signal to the fixing unit 700 via the wire provided below the mounting surface. The fixing unit 700 fixes the top plate 115 to the support frame 116 in response to the arrival of the object detection signal.

(Second Modification)

A difference between the second embodiment and the first modification is that the object detection unit 900 is provided on the ceiling corresponding to the top plate movement range at the back surface side of the gantry 100.

The object detection unit 900 is provided on the ceiling corresponding to the top plate movement range at the back surface side of the gantry 100. The object detection unit 900 is, for example, an infrared sensor or ultrasonic sensor. The range of object detection by the object detection unit 900 corresponds to the top plate movement range.

Figure 7:
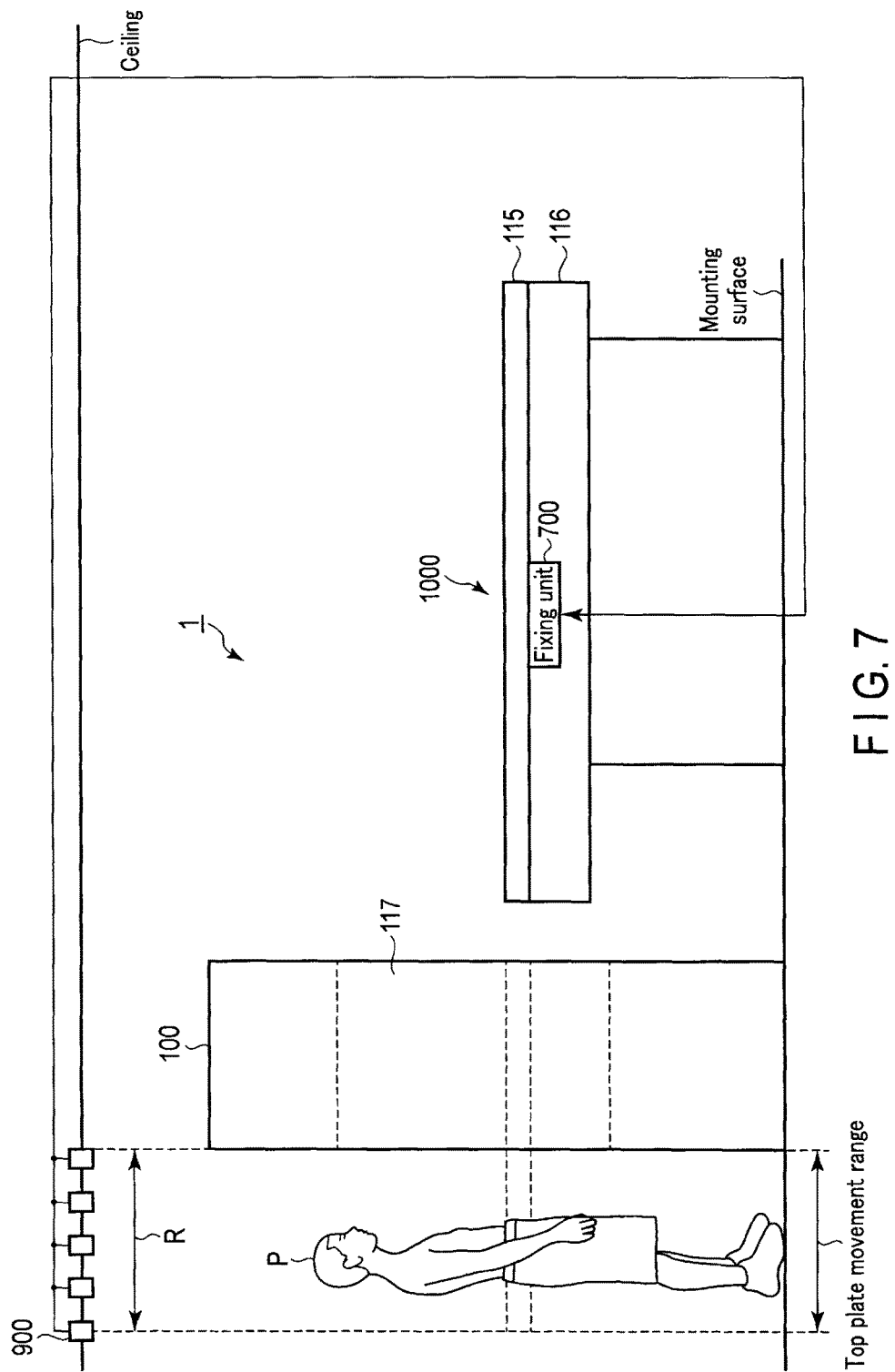
FIG. 7 is a view showing, together with the gantry and the bed, the subject P placed at the back surface side of the gantry according to the second modification of the second embodiment.
Figure 8:
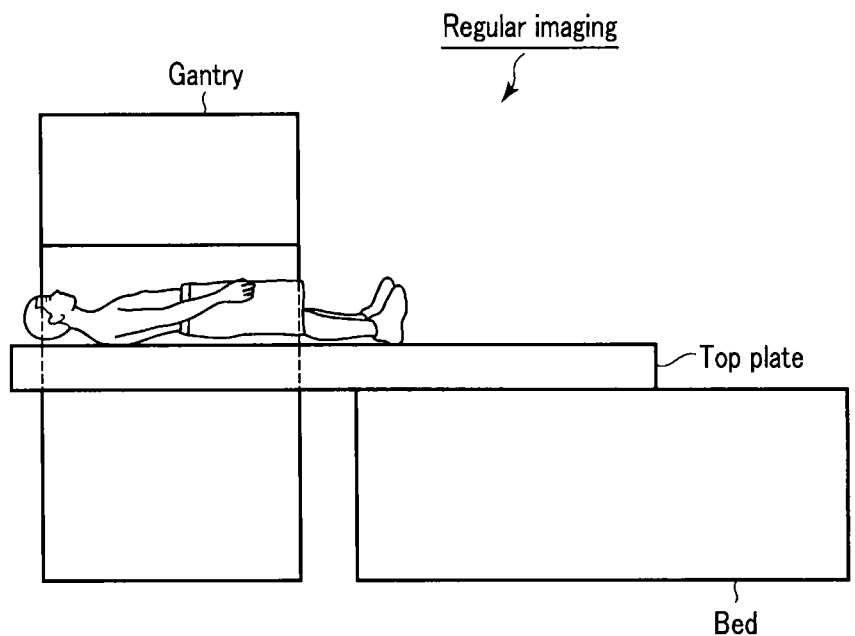
FIG. 8 is a schematic view showing an outline of an X-ray computed tomography apparatus concerning conventional regular imaging.
Figure 9:
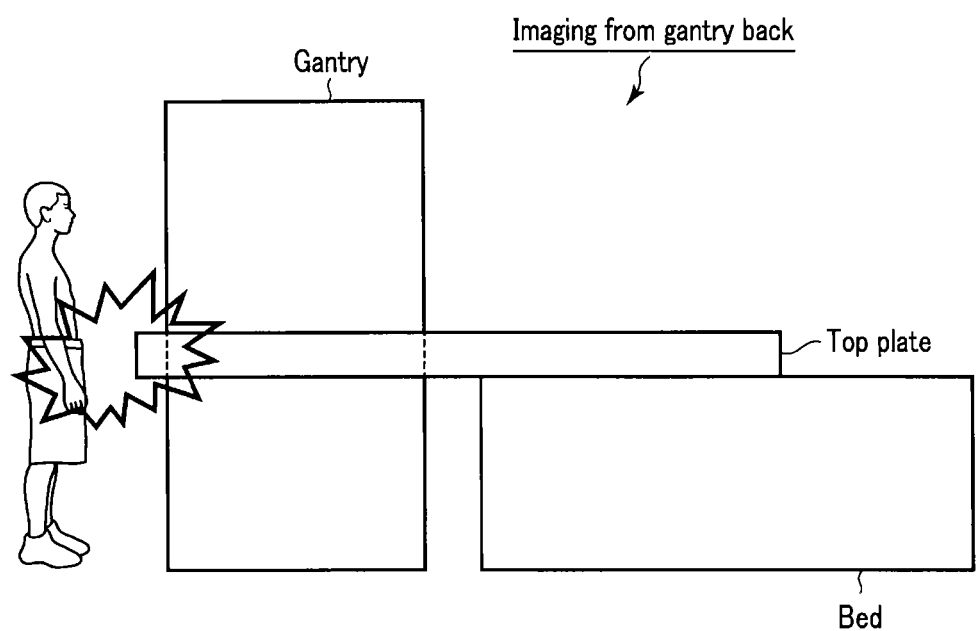
FIG. 9 is a view showing an example of how a subject placed at the gantry back is damaged when performing volume imaging of part of the subject at the gantry back according to the related art.

FIG. 7 is a view showing, together with the gantry 100 and the bed 1000, the subject P placed at the back surface side of the gantry 100. As shown in FIG. 7, when a subject P (or object) is placed within the top plate movement range, the object detection unit 900 provided on the ceiling at the back surface side of the gantry 100 detects the subject P (or object) in a detection range R. As shown in FIG. 7, the object detection unit 900 outputs an object detection signal to the fixing unit 700 via a wire provided inside the ceiling. The fixing unit 700 fixes the top plate 115 to the support frame 116 in response to the arrival of the object detection signal.

According to the above arrangement, the following effects can be obtained.

The X-ray computed tomography apparatus 1 according to this embodiment can detect an object arranged in the top plate movement range at the back surface side of the gantry 100 by using the object detection unit 900 provided at the back surface side of the gantry 100. According to the embodiment, the fixing unit 700 then can fix the top plate 115 to the support frame 116 in accordance with an object detection signal corresponding to the detection of the object. This makes it possible to secure the safety of a subject P when scanning a partial subject region upon inserting part of the subject P from the back surface side of the gantry 100 into the field of view.

In addition, combining this embodiment with the first embodiment improves the robustness concerning the fixation of the top plate 115 to the support frame 116 when performing a partial region scan. This further improves the safety of the subject P in a partial region scan.

In addition, when the technical idea of the X-ray computed tomography apparatus 1 according to this embodiment is to be implemented by a top plate control apparatus, the top plate control apparatus includes the constituent elements in a broken line 3 in the block diagram of FIG. 3. In this case, top plate fixing processing corresponds to the processes in steps Sb1 to Sb4 of the plurality of processes in the flowchart of FIG. 5. These processes are the same as those in the embodiments.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An X ray computed tomography apparatus, comprising:
a gantry including an X ray tube configured to generate X rays and an X ray detector configured to detect the X rays transmitted through a subject;
a bed arranged at a front surface side of the gantry and including a top plate configured to move toward an opening of the gantry;
input interface circuitry configured to receive input of an imaging plan concerning imaging of the subject; and
control circuitry configured to control the bed so that the top plate does not move to a back surface side of the gantry when the input interface circuitry receives the input of the imaging plan indicative of imaging a part of the subject inserted from the back surface side into the opening.

2. The X ray computed tomography apparatus of claim 1, wherein the bed comprises:
a support frame configured to movably support the top plate, and
a fixture including circuitry and configured to receive a subject detection signal, and in response, determine to fix the top plate to the support frame in accordance with the input of the imaging plan to image the part of the subject.

3. The X ray computed tomography apparatus of claim 2, further comprising a subject detector provided on the back surface side and configured to detect a predetermined subject placed at the back surface side, and, in response, send the subject detection signal to the fixture.

4. The X ray computed tomography apparatus of claim 3, wherein the detector is further configured to detect the subject placed in a movement range of the top plate at the back surface side.

5. The X ray computed tomography apparatus of claim 3, wherein the subject detector is provided on a mounting surface of the gantry at the back surface side and is further configured to detect the subject by touching of the subject.

6. The X ray computed tomography apparatus of claim 5, wherein the subject detector has a detection range corresponding to a movement range of the top plate at the back surface side of the gantry.

7. The X ray computed tomography apparatus of claim 3, wherein the subject detector is provided on one of an exterior of the gantry and a ceiling at the back surface side and is further configured to detect the subject by using one of a predetermined electromagnetic wave and a predetermined ultrasonic wave.

8. The X ray computed tomography apparatus of claim 3, further comprising display circuitry configured to display the input imaging plan received by the input interface circuitry, and
wherein the input interface circuitry receives input of a limit instruction to limit movement of the top plate.

9. A top plate control apparatus, comprising:
a bed arranged at a front surface side of a gantry and including a top plate configured to move toward an opening of a front surface side of the gantry;
input interface circuitry configured to receive input of an imaging plan concerning imaging of a subject; and
control circuitry configured to control the bed so that the top plate does not move to a back surface side of the gantry when the input interface circuitry receives the input of the imaging plan indicative of imaging a part of the subject inserted from the back surface side into the opening.

10. The top plate control apparatus of claim 9, wherein the bed comprises:
a support frame configured to movably support the top plate, and
a fixture including circuitry and configured to receive a subject detection signal, and in response, determine to fix the top plate to the support frame in accordance with input of the imaging plan to image the part of the subject.

11. A top plate control method, comprising:
inputting an imaging plan to image a part of a subject inserted into an opening of a gantry from a side on which no bed is arranged at one of two positions facing through the opening of the gantry; and
controlling the bed so that a top plate mounted on the bed does not move to the side, in response to the input of the imaging plan.

12. The top plate control method of claim 11, wherein the bed includes a support frame configured to movably support the top plate, and a fixture including circuitry and configured to receive a subject detection signal, and in response, determine to fix the top plate to the support frame in accordance with the input of the imaging plan to image the part of the subject.

* * * * *